Oct. 1, 1968 D. L. ARMSTRONG ET AL Plant Pat. 2,836
ROSE PLANT
Filed Feb. 27, 1967
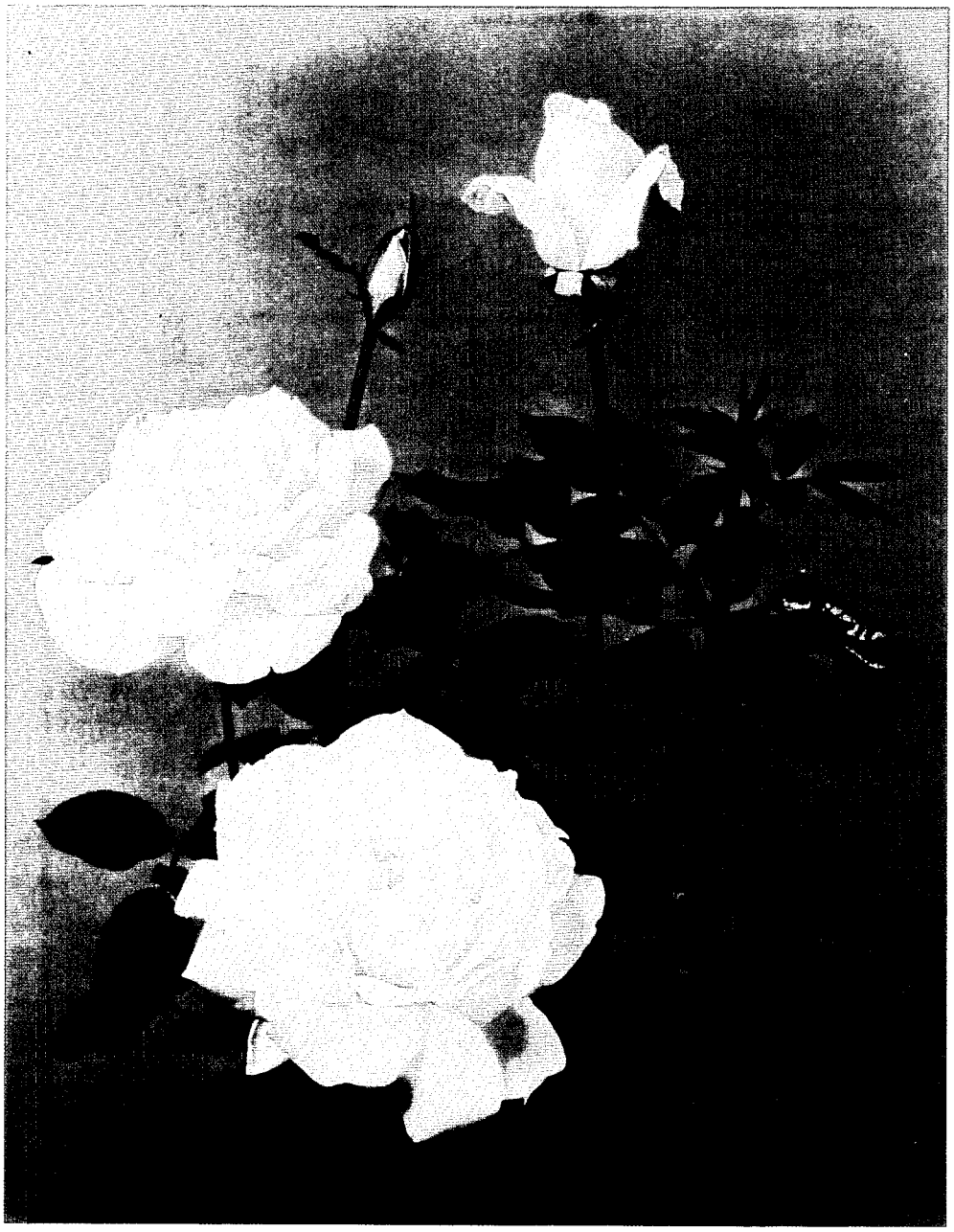
Inventors.
D. L. Armstrong
H. C. Swim
By: Robb & Robb
Attorneys.

United States Patent Office

Plant Pat. 2,836
Patented Oct. 1, 1968

2,836
ROSE PLANT

David L. Armstrong and Herbert C. Swim, Ontario, Calif., assignors to Armstrong Nurseries, Inc., Ontario, Calif., a corporation of California Filed Feb. 27, 1967, Ser. No. 619,079
1 Claim. (Cl. Plt.—15)

The present invention relates to a new and distinct variety of rose plant of the hybrid tea class, which was originated by us by crossing the rose variety known as "Helen Traubel" (Plant Patent No. 1,028) with an unnamed variety which is the subject of Plant Patent No. 1,254, the former being the seed parent and the latter being the pollen parent.

This new variety resulted from an extensive breeding program having for its primary objectives to produce improved rose varieties in the yellow to pink flowered color range, including blends of these colors, and combining as far as possible the excellent urn-shaped bud form and large flower size of "Helen Traubel" with the greater petalage and excellent plant habit of the unnamed pollen patent. Also desired was a strong flower fragrance which previous experience had shown to appear in a large number of seedlings derived from crosses using this pollen parent. These objectives were fully achieved, along with other desirable features, as evidenced by the following unique combination of characteristics which are outstanding in the new variety and which distinguish it from its parents, as well as from all other varieties of which we are aware:

(1) A moderately vigorous plant habit, with a semi-spreading or at least intermediate spreading to upright habit resembling that of "Helen Traubel" and sometimes more spreading than the latter;

(2) Relatively large, dark green, leathery, semi-glossy and disease resistant foliage;

(3) A quite floriferous habit, with the flowers borne generally singly on long and strong stems;

(4) A very attractive urn-shaped bud form and an excellent high-centered half-open and open flower form resulting in excellent exhibition type flowers;

(5) Large flowers with good petalage;

(6) A distinctive and attractive pale to light yellow flower color; and (7) A rich and strong flower fragrance which is unusual in yellow roses.

In comparison with its seed parent "Helen Traubel," the new variety has a light yellow flower color instead of the Apricot Pink and yellow blend of the flower color of this parent; it has considerably more flower petals than the average petalage of the parent; and the flowers of the new variety have a strong fragrance instead of the relatively mild fragrance of those of "Helen Traubel."

As compared with its unnamed pollen parent, the new variety has a more spreading plant habit and generally better and more consistent urn-shaped buds and half-open flowers, with the buds having more of an urn shape and being longer than the more fat and shorter buds of this parent.

Asexual reproduction of our new variety by budding, as performed at Ontario, Calif., shows that the foregoing characteristics and distinctions come true to form and are established and transmitted through succeeding propagations.

The accompanying drawing shows typical specimens of the vegetative growth and flowers of our new variety in different stages of development, with some of the flowers and vegetative growth being depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as (W)) and Robert Ridgeway's Color Standards and Nomenclature (hereinafter abbreviated as (R)), as indicated:

Type: Bush; outdoor; seedling; for cut flowers and for garden decoration.
Class: Hybrid tea.
Breeding: Seedling.
*Seed parent.*—"Helen Traubel."
*Pollen parent.*—An unnamed seedling.
Propagation: Holds its distinguishing characteristics through succeeding propagations by budding.

*Flower*

Locality where grown and observed: Ontario, Calif.
Flowers borne: Usually singly, but sometimes three or four to stem; in irregular clusters; on strong, long stems.
Quantity of bloom: Free, outdoors.
Continuity: Nearly continuous during growing season.
Fragrance: Strong. Nature—spicy.
Bud:
*Peduncle.*—Long; heavy; erect; smooth; with several small stipitate glands and from none to few small prickles. Color—near Mignonette Green, Plate XXXI (R), overlaid with near Buffy Olive, Plate XXX (R) on side exposed to the sun.
*Before calyx breaks.*—Size—large. Form—from medium length to long; pointed and ovoid.
*As calyx breaks.*—Color—between Uranium Green, Plate 63/1, page 63 (W) and Dresden Yellow, Plate 64/1, page 64 (W).
*Sepals.*—Usually with foliaceous appendages extending from ⅓ to ½ of sepal length. Inner surface—with fine, wooly tomentum. Outer surface—usually smooth. Alternate margins—lined with fine, wooly tomentum. Other margins—with several to many small stipitate glands and small, slender foliaceous parts.
*As first petal opens.*—Size—from average to large. Form—from medium length to long; ovoid; urn-shaped. Color: outside—near Primrose Yellow, Plate 601/2, page 65 (W), blending with near Dresden Yellow, Plate 64/1, page 64 (W) toward base of petal; inside—between Primrose Yellow, Plate 601/3, page 65 (W) and Empire Yellow, Plate 603/3, page 66 (W), blending with near Dresden Yellow, Plate 64, page 64 (W) toward base of petal.
*Opening.*—Opens up well; is not retarded or prevented from opening by cold, hot, wet or dry weather.
Bloom:
*Size (when fully open).*—Large; from 4½ inches to 5½ inches.
*Petalage.*—Double; from 30 to 35 petals, plus 8 to 10 petaloids; arranged irregularly.
*Form.*—High-centered at first, but becoming cupped to high-centered; petals being at first tightly cupped, with tips reflexed outward, but later becoming more loosely flat to cupped, with tips reflexed outward at maturity; outside and intermediate pedals of both newly opened and three-days open flowers being reflexed outward both along apex and edges of petals, and outside petals usually being reflexed more strongly outward both along apex and edges of petals.
Petals:
*Texture.*—Medium thickness; moderately soft.

*Appearance.*—Inside—satiny. Outside—satiny.

*Shape.*—Outside—broadly obovate, with apex flat and sometimes with 1 or 2 notches. Intermediate—obovate, with apex rounded and sometimes with 1 or 2 notches. Inside—obovate, with apex rounded.

This description of a newly opened flower was made from a rose grown outdoors during the month of October at Ontario, Calif.:

*Color.*—Outer petal: outside surface—between white and Primrose Yellow, Plate 601/3, page 65 (W), blending with near Primrose Yellow, Plate 601/1, page 65 (W) toward base of petal; inside surface—between white and Primrose Yellow, Plate 601/3, page 65 (W), blending with near Primrose Yellow, Plate 601, page 65 (W) toward base of petal. Intermediate petal: outside surface—same as outer petal; inside surface—same as outer petal. Inner petal: outside surface—between Primrose Yellow, Plate 601/3, page 65 (W) and Empire Yellow, Plate 603/3, page 66 (W), blending with near Empire Yellow, Plate 603, page 66 (W) toward base of petal; inside surface—same as outside surface.

This description was made from a rose that was open for three days outdoors during the month of October at Ontario, Calif.:

*Color.*—Outer petal: outside surface—between white and Primrose Yellow, Plate 601/3, page 65 (W), blending with near Primrose Yellow, Plate 601/2, page 65 (W) toward base of petal; inside surface—same as outside surface. Inner petal: outside surface—same as outer petal; inside surface—same as outer petal.

*General color effect.*—Newly opened flower—between Primrose Yellow, Plate 601/3, page 65 (W) and Empire Yellow, Plate 603/1, page 66 (W). Three days open—between white and Empire Yellow, Plate 603/3, page 66 (W).

*Behavior.*—Drop off cleanly; not particularly affected by cold, hot, wet or dry weather.

*Flower longevity.*—On bush in garden—4 or 5 days in November. Cut roses grown outdoors and kept at living-room temperatures—3 or 4 days in November.

*Reproductive organs*

Stamens: Many; arranged regularly about pistils; a few mixed with petaloids.

Filaments: Medium length (from 6 mm. to 12 mm. long); most with anthers. Color—near Buttercup Yellow, Plate 5/1, page 5 (W).

Anthers: From small to medium size; all open approximately at once. Color: upper side—margins near Saffron Yellow, Plate 7/1, page 7 (W), with remainder near Aureolin, Plate 3/2, page 3 (W); under side—margins near Saffron Yellow, Plate 7/1, page 7 (W), with remainder near Aureolin, Plate 3/2, page 3 (W).

Pollen: Moderately abundant. Color—near Cadmium Orange, Plate 8/1, page 8 (W).

Pistils: Many (approximately 130).

Styles: Moderately even; average length; thin; bunched. Color—upper ¼ of style near Cherry, Plate 722/1, Base—round. Margin—simply serrate.
Plate 1/3, page 1 (W).

Stigma: Color—near Yellow Ochre, Plate 07/3, page 101 (W).

Ovaries: Usually all enclosed in calyx.

Hips: Average length; globular; smooth; walls thick and fleshy. Color (half mature)—near Rainette Green, Plate XXXI (R).

Sepals: Falling soon; medium length; straight. Color: inside—near Grape Green, Plate XLI (R); outside—near Rainette Green, Plate XXXI (R).

Seeds: Few (from 8 to 20), medium size.

*Plant*

Foliage:

*Leaves.*—Compound of usually 3 to 7 leaflets; abundant; large; leathery; semi-glossy.

*Leaflets.*—Shape—broadly oval, with apex acute. Base—round. Margin—simply serrate.

*Color.*—Mature: upper surface—between Forest Green, Plate XVII (R) and Empire Green, Plate XXXII (R); under surface—near Chromium Green, Plate XXXII (R). Young: upper surface—near Cress Green, Plate XXXI (R); under surface—near Asphodel Green, Plate XLI (R).

*Rachis (the supporting stem of the compound leaf).*—Heavy. Upper side—grooved; with several to many stipitate glands on edges. Under side—smooth; with none to few stipitate glands and none to few small prickles.

*Stipules.*—From medium length to long; from medium width to wide; with short points turning out at an angle of more than 45°.

*Disease resistance.*—Better than average resistance to mildew, as determined by comparison with other varieties now in commerce and grown under comparable conditions at Ontario, Calif.

Growth:

*Habit.*—From upright to spreading; much-branched.

*Growth.*—Moderately vigorous.

*Canes.*—From medium caliper to heavy.

*Main stems.*—Color—near light Yellowish-Olive, Plate XXX (R). Large prickles—several; medium length; hooked slightly downward; with short to medium length, narrow base; color—near Sayal Brown, Plate XXIX (R). Small prickles—from none to few; color—near Sayal Brown, Plate XXIX (R). Hairs—none.

*Branches.*—Color—near Mignonette Green, Plate XXXI (R). Large prickles—several; medium length; hooked slightly downward; with short to medium length, narrow base; color—near Snuff Brown, Plate XXIX (R). Small prickles—from none to few; color—near Snuff Brown, Plate XXIX (R). Hairs—none.

*New shoots.*—Color—near Apple Green, Plate XVII (R), overlaid with near Walnut Brown, Plate XXVIII (R) on side exposed to the sun. Large prickles—several; medium length; hooked slightly downward, with short to medium length, narrow base; color—near Indian Red, Plate XXVII (R). Small prickles—from none to few; color—near Indian Red, Plate XXVII (R). Hairs—none.

We claim:

1. A new distinct variety of rose plant of the hybrid tea class, substantially as herein shown and described, characterized particularly as to novelty by the unique combination of a moderately vigorous plant habit, with a semi-spreading or at least intermediate spreading to upright habit resembling that of "Helen Traubel" and sometimes more spreading than the latter, relatively large, dark green, leathery, semi-glossy and disease resistant foliage, a quite floriferous habit, with the flowers borne generally singly on long and strong stems, a very attractive urn-shaped bud form and an excellent high-centered half-open and open flower form resulting in excellent exhibition type flowers, large flowers with good petalage, a distinctive and attractive pale to light yellow flower color, and a rich and strong flower fragrance which is unusual in yellow roses.

No references cited.

ROBERT E. BAGWILL, *Primary Examiner.*